United States Patent [19]

Kahan

[11] Patent Number: 4,518,608

[45] Date of Patent: May 21, 1985

[54] WATERSOLUBLE DERIVATIVES OF NON-STEROIDAL ANTI-INFLAMMATORY AGENTS AND A PROCESS FOR THE PRODUCTION THEREOF

[75] Inventor: Agostne Kahan, Budapest, Hungary

[73] Assignee: Medimpex Gyogyszerkuelkereskedelmi Vaallalat, Budapest, Hungary

[21] Appl. No.: 486,861

[22] Filed: Apr. 20, 1983

Related U.S. Application Data

[63] Continuation of Ser. No. 189,008, Sep. 22, 1980, abandoned.

[30] Foreign Application Priority Data

Sep. 27, 1979 [HU] Hungary .............................. KA 1539

[51] Int. Cl.$^3$ ............................................... A61K 31/40
[52] U.S. Cl. .................................................... 514/420
[58] Field of Search .......................................... 424/274

[56] References Cited

U.S. PATENT DOCUMENTS

| 3,161,654 | 12/1964 | Shen | 424/274 |
| 3,461,208 | 8/1969 | Winter | 424/274 |
| 3,557,279 | 1/1971 | Morse | 424/274 |
| 4,440,778 | 4/1984 | Matsui et al. | 424/274 |
| 4,442,118 | 4/1984 | Dvornik et al. | 424/274 |

FOREIGN PATENT DOCUMENTS

| 0002976 | 10/1981 | European Pat. Off. | 424/274 |
| 0087655 | 9/1983 | European Pat. Off. | 424/274 |

OTHER PUBLICATIONS

Chem. Abstracts 94:7725q (1981).
Chem. Abstracts 85:182343z (1976).
Sears et al., Pharmacology of the Eye, Springer Edition, N.Y. 1984, p. 543.
Srinivasan: Ocular Therapeutics, Masson Edition, N.Y. 1982, pp. 73–78.
Billups et al., American Drug Index, p. 311, 1982.
Goodman et al., Pharmacological Basis of Therapeutics, 6th Edition, pp. 705–707.
Physicians Desk Reference, 1981, 35th Edition, "Indocin", p. 1210.
Physicians Desk Reference, 1984, 38th Edition, "Indocin", p. 1291.

*Primary Examiner*—Ethel G. Love
*Attorney, Agent, or Firm*—Karl F. Ross; Herbert Dubno

[57] ABSTRACT

The invention relates to watersoluble derivatives of non-steroidal anti-inflammatory drugs and also to therapeutic compositions containing these derivatives.

5 Claims, No Drawings

WATERSOLUBLE DERIVATIVES OF NON-STEROIDAL ANTI-INFLAMMATORY AGENTS AND A PROCESS FOR THE PRODUCTION THEREOF

This application is a continuation of application Ser. No. 189,008 filed Sept. 22, 1980, now abandoned.

BACKGROUND OF THE INVENTION

Non-steroidal anti-inflammatory agents are increasingly used in clinical practice to cure degenerative joint diseases or arthritis and they are used for the treatment of inflammatory locomotor diseases, gout, spondilitis and related diseases. The therapeutic agents are classified in the literature according their chemical character. The common chemical feature of the therapeutic agents used in this invention is an aromatic nucleus with a hydrophobic side-chain (or side-chains) and an acidic group (a carboxylic group). The compounds are hydrophobic (lipophilic) water-insoluble. The oldest representatives on non-steroidal anti-inflammatory drugs are the salicylic acid derivatives, the newer ones are the following:
   anthranilic acid derivatives,
   indol derivatives,
   naphthalene derivatives,
   other arylcarboxylic acid derivatives.

The parent compounds are insoluble in water, some of the derivatives rapidly decompose in alkaline solutions; thus injectable solutions or other aqueous compositions are not used for therapeutic purposes. Oral administration in the form of tablets, capsules, syrups are usually employed or suppositories are used for the therapy of different diseases in internal medicine, rheumatology, dermatology, stomatology, ophthalmology, surgery, gynecology etc. The wide-spread use in therapy made necessary the production of intestinosolvent drugs. On the other hand, efforts were made to produce water-soluble derivatives of the hydrophobic compounds to enhance absorption, to reduce the effective dose and hereby side-effects.

Indomethacin, well known since 1963 is used in clinical practice since 1965 for its efficient analgesic, anti-inflammatory and antipyretic properties. Since indomethacin exhibits several undesirable side-effects after oral administration, the search for new therapeutic anti-inflammatory drugs has continued. Anti-inflammatory agents devoid of nitrogen cause less severe side-effects, but their synthesis per se did not solve the occurrence of potentially very grave adverse effects.

It is well known that part of the adverse effects of the parent compounds cannot be separated from their therapeutic effect. The anti-inflammatory drugs inhibit enzymes participating in the metabolism of intact tissues also in vitro [Vane, J. R.: Inhibition of prostaglandin synthesis as a mechanism of action of aspirin-like drugs. Nature New Biology 231, 232, 1971]. The most known and most often occurring side-effect is the eroding of the gastric mucosa, which is enhanced by the oral administration of the anti-inflammatory drug. Synthesis of prostaglandin causing inflammation decreases and the mucosa becomes more vulnerable.

Several investigations were performed for the application of anti-inflammatory drugs in an aqueous medium (to produce suspensions and solutions) by means of combining anti-inflammatory agents with different compounds, therapeutic vehicles or surface-active agents. To increase dissolution of indomethacin, flufenamic acid or mefenamic acid, Dambis-Khahl suggested the addition of urea and 4-dimethylamino-2,3-dimethyl-1-phenyl-pirrazolidon-5-on [Can. J. Pharm. Sci. 11, 114–117, 1976]. Krusko, E. [Farmaco Ed. Pract. 31, 463–472, 1976] suggested to use nonionic polyoxyethylene type surface-active agents for the dissolution of indomethacin. Ford, Rubinstein et al. [Pharm. Acta Helv. 53, 93–98, 1978] studied the interaction of indomethacin and polyethylene glycol (6000). A suspension can be prepared by mixing 85 percent of polyethylene glycol and 15 percent of indomethacin. El Sabbagh, Chanem et al. [Pharmazie 33, 529–531, 1978] studied the interaction of nonionic (Tween type) surface active compounds, indomethacin and urea to increase water solubility of the therapeutic agent. Sanghavi and Kalib [Ind. J. Pharm. Sci. 40, 239, 1978] use pentaerythritol for the aqueous suspension of indomethacin. Pawolczyk, E., Knitter, B. [Kinetics of drug degradation. Part 58: Method of preparation and stability of 3% aqueous indomethacin solution. Pharmazie 33, 586–588, 1978] produced a stable aqueous solution containing 3 percent of indomethacin, by means of boiling the therapeutic agent with ethylurea and ethylcarbamate. The so obtained diluted solutions, however, did not come into general use. Hamada et al. [Chem. Pharm. Bull. 23, 1205-11, 1975] made efforts to increase the dissolution of flufenamic acid and mefenamic acid using different auxiliary agents.

In spite of the great number of experiments there is no suitable method known for the intravenous, intramuscular, local, intraarticular, subconjunctival administration or for the distillation of eye-drops of non-steroidal acidic anti-inflammatory agents. The size of dose and the degree of side-effects thereof could not be changed therefore to date.

The object of the invention is the production of water-soluble derivatives of non-steroidal acidic anti-inflammatory agents suitable for therapeutic use, especially for peritoneal or other injection and suitable for local application. Thereby the therapeutic range of these agents can be increased, the size of dose can be decreased maintaining the efficacy of these agents. The administration of these agents is allowed also in those cases where the basic compounds could not be used due to undesirable side-effects. The application of these agents is possible also in those acute cases where a greater dose assures a rapid thereapeutic efficacy and recovery of the patient.

According to the invention non-steroidal acidic anti-inflammatory agents comprise those compounds which have an aromatic nucleus with one or more hydrophobic side-chains and an acidic (carboxylic) group, and can be classified according the following:
(a) salicylic acid derivatives: aspirin (acetylsalicylic acid);
(b) anthranilic acid derivatives: flufenamic acid 2-[3-(trifluoromethyl)anilino]-benzoic acid niflumic acid 2-[3-(trifluoromethyl)anilino]nicotinic acid mefenamic acid N-(2,3-xylyl)anthranilic acid
(c) indol derivatives: indomethacin 1-(p-chlorobenzoyl)-5-methoxy-2-methyl-indole-3-acetic acid;
(d) naphthalene derivatives: naproxen d-2-(6-methoxy-2-naphthyl)propionic acid;
(e) other arylcarboxylic acids: aclofenac 4-allyloxy-3-chlorophenylacetic acid; fenoprofen α-dl-2-(3-phenoxylphenyl)propionic acid; ibuprofen (2-(4-isobutylphenyl)propionic acid); ketoprofen (2-(3-benzoylphenyl)propionic acid); phenbuphen ((3,4-biphenyl)carbonyl propionic acid); metizianic acid (10-methyl-2-phenothiazinyl acetic acid).

To prepare the watersoluble derivatives of the anti-inflammatory agents the following hydrophilic compounds are used:

| | |
|---|---|
| [tris(hydroxymethyl)aminomethane] | (TRIS) |
| [bis(2-hydroxyethyl)-amino]tris(hydroxymethyl)methane] | (BIS-TRIS) |
| {1,3-bis[tris(hydroxymethyl)methylamino]-propane} | (BIS-TRIS-PROPANE) |
| 3-{[tris(hydroxymethyl)methyl]amino}-propane-sulfonic acid | (TAPS) |
| 2-{[tris(hydroxymethyl)methyl]amino}-ethane-sulfonic acid | (TES) |
| N—[tris(hydroxymethyl)methyl]glycine | (TRICINE) |

According to the invention the watersoluble derivatives of the anti-inflammatory agents contain at least one mole of the hydrophilic compound per mole of anti-inflammatory drug; in general the latter can be used also in excess over this equimolar quantity.

The novel watersoluble derivatives of the acidic anti-inflammatory agents are produced by means of contacting the anti-inflammatory agent with the hydrophylic component or its solution which can be an aqueous or a solution in a suitable organic solvent. Expediently the hydrophilic compound is dissolved in water or in a polar organic solvent and thereafter the anti-inflammatory agent is added. The new derivative can be separated, if necessary, by evaporating the solvent or the water in vacuo. The so obtained residue forms the compound to be used for therapeutic purposes.

The invention comprises those therapeutic compositions and the production thereof, which contain an above mentioned non-steroidal acidic anti-inflammatory agent and a hydrophylic compound in a suitable molar ratio with adjuvants or ingredients.

For the purpose of local treatment the solutions of the non-steroidal acidic anti-inflammatory agents are incorporated into eye-drops or ointments. In these compositions generally the therapeutically active compounds compatible with the therapeutic agents of the invention can be used as well.

The novel therapeutic compositions can be employed as anti-inflammatory, antipyretic and analgesic drugs. They inhibit prostaglandin synthetase activity in vitro. The concentrations of the aqueous solutions of the above mentioned drugs are 10–100 mg./ml. or above, pH values of the solutions are about 6.8–8.5. The compounds produced according to the invention can be stored in the form of a powder for years.

The derivatives according to the invention can be applied intravenously, intramuscularly, intraarticularly, subconjunctivally or in the form of eye-drops. It is highly advantageous that the instant derivatives are readily soluble in water and lipids as well; e.g. the partition coefficient (K) of the derivative according to the invention of indomethacin in chloroform/water is 1.0. This favorable partition coefficient ensures diffusion of the therapeutically active compound through the cell membrane and ensures thereby constant high tissue level. Derivatives prepared according to the invention are bound presumably in the blood vessels to serum albumin similar to the parent compounds and they exert no tissue damaging effect. The derivatives prepared according to the invention and administered intravenously proved to be 4-times more effective in the carrageen induced edema test than the parent compound after oral administration.

SPECIFIC EXAMPLES

The application of the present invention to different nonsteroidal anti-inflammatory drugs and route of administration is exemplified but not limited to the following Examples.

EXAMPLE 1

Composition for therapeutic use is prepared from the following compounds:

| | |
|---|---|
| Dry fill | 25 mg. indomethacin |
| Dissolving ampoule | 50 mg. TRIS in 2 ml. distilled water. |

After having dissolved the dry fill in the solvent, the final pH is 6.8. The so obtained solution inhibits prostaglandin synthetase activity by 90 percent.

The therapeutic agent is non-irritant can be applied intravenously, intramuscularly, intraarticularly, subconjunctivally or as eye-drops.

Steril purulance in the aqueous humour, a consequence of increased permeability is diminished by instalation of eye-drops or subconjunctival injection. Injection of arachidonic acid into rabbit eye increased protein content of the aqueous humour 10-fold in consequence of the increased permeability. After pretreatment of the fellow eye with indomethacin eye drops the aqueous humour prevailed normal protein content.

EXAMPLE 2

For the isolation of watersoluble indomethacin derivative 1000 g. of indomethacin are dissolved in 10 liter of methanol with constant stirring at room temperature and thereafter 1000 g. TRIS in 1 liter of methanol are added. The so obtained solution is slightly heated and evaporated in vacuo. Care must be taken not to exceed 20° C. The so obtained white crystalline compound can easily be dissolved in water. In a concentration of 100 mg./ml. the pH is 6.4. The melting point of the compound is 148° C. after recrystallization from acetone-ethylether.

The therapeutic composition can be used according to Example 1. It can be used also in a mixture with suitable ingredients orally when filled in capsules.

EXAMPLE 3

For ophthalmological purposes 50 mg. of indomethacin, 36 mg. of TRIS, 10 mg. of citric acid and 10 mg. of boric acid are mixed and the dry mixture is filled into capsules. The content of the capsules can be dissolved in 10 ml. of water. The pH of the so obtained solution is 7.3 and the solution is isotonic. The solution can be used as eye-drops.

EXAMPLE 4

Ointment for local treatment is made up by preparing 1 ml. solution of the indomethacin derivative according to Example 1, and by mixing the so obtained aqueous solution with 0.045 g. of cholesterol, 0.090 g. of paraffine oil and 2.895 g. of yellow liquid paraffine. The indomethacin ointment has a local anti-inflammatory activity and can be used as a sun-cream.

EXAMPLE 5

The indomethacin solution prepared according to Example 1 is lyophilized. After dissolving the dry residue in 1 ml. of water, the obtained solution can be used for similar therapeutic purposes as mentioned in Example 1.

EXAMPLE 6

A pharmaceutical compositions is prepared from the following components:

| | |
|---|---|
| Dry fill | 50 mg. indomethacin |
| Dissolving ampoule | 80 mg. N—[tris(hydroxymethyl)-methyl] glycine (TRICINE) |
| | 2 ml. distilled water |

Administration: as in Example 1.

EXAMPLE 7

A pharmaceutical composition is prepared from the following components:

| | |
|---|---|
| Dry fill | 50 mg. indomethacin |
| Dissolving ampoule | 70 mg. 1,3-bis[tris(hydroxymethyl)-methylamino]-propanesulfonic acid |
| | 10 mg. sodium pyrosulfite |
| | 30 mg. polyvinyl pyrrolidone |
| | 2 ml. distilled water |

Administration: same as in Example 1.

EXAMPLE 8

A therapeutic composition is prepared from the following components:

| | |
|---|---|
| Dry fill | 50 mg. indomethacin |
| Dissolving ampoule | 120 mg. 3-[tris(hydroxymethyl)-methylamino]ethanesulfonic acid |
| | 2 mg. sodium pyrosulfite |
| | 20 mg. polyvinyl alcohol |
| | 2 ml. distilled water |

Administration: as in Example 1.

EXAMPLE 9

A pharmaceutical composition is prepared from the following components:

| | |
|---|---|
| Dry fill | 230 mg. naproxen d-2-(6'-methoxy-2'-naphthyl)-propionic acid |
| Dissolving ampoule | 360 mg. TRIS |
| | 10 ml. distilled water |

After having dissolved the dry fill in the solvent, the final pH=8.0. Administration: as in Example 1.

EXAMPLE 10

Watersoluble naproxen is isolated by dissolving 230 mg. of naproxen in 5 ml. of methanol and 180 mg. of TRIS and by subsequent evaporating the solvent at 25° C. When the dry residue is dissolved in 10 ml. of water, the pH is 8.0. The clear solution can be stored for 1 week at 4° C., without reduction of the therapeutic efficacy.

EXAMPLE 11

For the production of watersoluble niflumic acid 2800 mg. of niflumic acid (2-[3-trifluoromethyl)anilino]-nicotinic acid are dissolved in 500 ml. of methanol, and 3600 mg. of TRIS in 400 ml. of methanol are added. After complete dissolution the solution is filled up to 1000 ml. 50-50 ml. samples are evaporated in vacuo. The dry residues are equivalent to 140 mg. niflumic acid each. The dry residue can be stored at room temperature for years without reduction of efficacy.

The dry residue can be dissolved in 2.5 ml. of distilled water and can be administered parenterally. The aqueous solution can be stored at 4° C. for 1 week without reduction of efficacy.

EXAMPLE 12

A pharmaceutical composition is prepared from the following components:

| | |
|---|---|
| Dry fill | 50 mg. fenoprofen (α-dl-2-(3-phenoxyphenyl)propinic acid) |
| | 72 mg. ethylenediamine-tetra-acetic acid |
| Dissolving ampoule | 144 mg. TRIS |
| | 2 ml. distilled water |

After having dissolved the dry fill in the solvent, the pH is 7.2. Administration: as in Example 1.

EXAMPLE 13

A pharmaceutical composition is prepared from the following components:

| | |
|---|---|
| Dry fill | 230 mg. naproxen [d-2-(6'-methoxy-2'-naphthyl)-propionic acid] |
| Dissolving ampoule | 430 mg. BIS-TRIS-PROPANE |
| | 10 ml. distilled water |

After having dissolved the dry fill in the solvent, the pH is 7.9. Administration: as in Example 1.

EXAMPLE 14

A pharmaceutical composition is prepared from the following compounds:

| | |
|---|---|
| Dry fill | 200 mg. acetylsalicylic acid |
| Dissolving ampoule | 790 mg. TRIS |
| | 10 ml. distilled water |

After having dissolved the dry fill in the solvent, the final pH is 7.8. The solution can be administered as in Example 1. The dry fill can be filled in capsules and administered orally.

What we claim is:

1. A water-soluble, analgesic, anti-inflammatory, antipyretic or antiphlogistic pharmaceutical composition suitable for parenteral administration comprising an analgestic, anti-inflammatory, antipyretic or antiphlogistic effecitve amount of indomethacin and a hydrophilic compound selected from the group which consists of TRIS, BIS-TRIS, BIS-TRIS-PROPANE, TAPS, TES, TRICINE and mixtures thereof.

2. The pharmaceutical composition defined in claim 1 wherein at least one mole of the hydrophilic compound is present per mole of indomethacin.

3. An analgesic, anti-inflammatory, antipyretic or antiphlogistic method of treatment which comprises the step of parenterally administering to an animal subject in need of analgesic, anti-inflammatory, antipyretic and antiphlogistic treatment, an analgesic, anti-inflammatory, antipyretic or antiphlogistic effective amount of the water-soluble pharmaceutical composition defined in claim 1.

4. The method of treatment defined in claim 3 wherein the parenteral administration is intravenous, intramuscular, or intraarticular administration.

5. A method of treating inflammation of the eye which comprises the step of subconjunctively or locally administering to an animal subject in need of treatment for eye inflammation, an anti-inflammatorily effective amount of the water-soluble pharmaceutical composition defined in claim 1.

* * * * *

UNITED STATES PATENT AND TRADEMARK OFFICE
CERTIFICATE OF CORRECTION

PATENT NO. : 4,518,608
DATED : 21 May 1985
INVENTOR(S) : Agostne KAHAN

It is certified that error appears in the above-identified patent and that said Letters Patent is hereby corrected as shown below:

In the heading, left column, [73] should be omitted.

Signed and Sealed this

Twenty-sixth Day of November 1985

[SEAL]

Attest:

Attesting Officer

DONALD J. QUIGG

Commissioner of Patents and Trademarks